United States Patent [19]

Haruta et al.

[11] Patent Number: 5,623,090
[45] Date of Patent: Apr. 22, 1997

[54] METHOD FOR PRODUCTION OF ALCOHOL, KETONE, AND EPOXIDE BY OXIDATION OF HYDROCARBON

[75] Inventors: Masatake Haruta, Ikeda; Susumu Tsubota, Ashiya; Toshio Hayashi, Kobe, all of Japan

[73] Assignee: Agency of Industrial Science & Technology, Ministry of International Trade & Industry, Tokyo, Japan

[21] Appl. No.: 547,812

[22] Filed: Oct. 25, 1995

[30] Foreign Application Priority Data

Oct. 28, 1994 [JP] Japan .................................. 6-289008

[51] Int. Cl.$^6$ .................................................. C07C 45/33
[52] U.S. Cl. ........................ 568/360; 568/401; 549/523; 549/533
[58] Field of Search .................................... 549/523, 533; 568/401, 360

[56] References Cited

U.S. PATENT DOCUMENTS

| | | | |
|---|---|---|---|
| 2,398,612 | 4/1946 | Bergsteinsson et al. | 568/401 |
| 3,485,877 | 12/1969 | Hargis et al. | 568/401 |
| 3,723,352 | 3/1973 | Alexander et al. | 568/401 |
| 4,698,324 | 10/1987 | Haruta et al. | 502/243 |
| 4,839,327 | 6/1989 | Haruta et al. | 502/243 |
| 4,937,219 | 6/1990 | Haruta et al. | 502/243 |
| 5,051,394 | 9/1991 | Haruta et al. | 502/324 |

FOREIGN PATENT DOCUMENTS 616422 1/1994 Japan .
629137 4/1994 Japan .

OTHER PUBLICATIONS

J. Chem. Soc., Chem. Commun., pp. 731–733, 1983, Derek H.R. Barton, et al., "Activation of The C–H Bond in Hydrocarbons: The Isolation and Catalytic Activity of a Trinuclear Organoiron Carboxylate Cluster".

Bull. Chem. Soc. Japan, vol. 64, No. 8, pp. 2513–2518, 1991, Toshihiro Takai, et al., "Aerobic Epoxidation of Olefinic Compounds Catalyzed by Tris(1,3–Diketonato)Iron(III)".

J. Chem. Soc. Chem. Commun., pp. 1446–1447, 1992, T. Tatsumi, et al., "Hydroxylation of Benzene and Hexane by Oxygen and Hydrogen Over Palladium–Containing Titanium Silicalites".

J. Am. Chem. Soc., vol. 109, No. 9, pp. 2387–2389, 1987, Norman Herron, et al., "A Highly Selective Zeolite Catalyst for Hydrocarbon Oxidation. A Completely Inorganic Mimic of the Alkaneω–Hydroxylases".

Database WPI, Derwent Publications, AN–94–061881, JP–A–06–016422, Jan. 25, 1994.

Primary Examiner—James H. Reamer
Attorney, Agent, or Firm—Oblon, Spivak, McClelland, Maier & Neustadt, P.C.

[57] ABSTRACT

An alcohol or a ketone or a mixture thereof is produced from a saturated hydrocarbon or an epoxide is produced from an unsaturated hydrocarbon by passing a mixture comprising of molecular hydrogen, the saturated or unsaturated hydrocarbon and oxygen through a bed of a catalyst comprising a titanium dioxide carrier and ultrafine gold particles deposited on the carrier, thereby effecting the oxidation of the hydrocarbon with oxygen.

7 Claims, No Drawings

METHOD FOR PRODUCTION OF ALCOHOL, KETONE, AND EPOXIDE BY OXIDATION OF HYDROCARBON

BACKGROUND OF THE INVENTION

1. Field of the Invention

This invention relates to a method for the production of an alcohol and/or a ketone from a saturated hydrocarbon and an epoxide from an unsaturated hydrocarbon by the oxidation with oxygen of the hydrocarbon using of a gold-titanium dioxide-containing solid catalyst in the presence of hydrogen.

2. Description of the Prior Art

The method for converting a hydrocarbon into a compound containing oxygen by the use of oxygen is a very advantageous technique and has provided the modern chemical industry with numerous benefits. It has been held, however, that, with a few exceptions, direct production of an alcohol and a ketone from a saturated hydrocarbon and an epoxide from an unsaturated hydrocarbon is generally difficult. The only industrial-scale application of the technique for converting a saturated hydrocarbon into an alcohol and a ketone by the use of molecular oxygen as an oxidizing agent, for example, has been in the production of cyclohexanol and cyclohexanone from cyclohexane as the starting material. While the technique for conversing an unsaturated hydrocarbon into an epoxide has been put to use on an industrial scale for the production of ethylene oxide from ethylene, the production of epoxides from other unsaturated hydrocarbons, such as the synthesis of propylene oxide from propylene, is generally difficult to attain.

Previously reported techniques for the conversion of a saturated hydrocarbon into an alcohol and a ketone and the conversion of an unsaturated hydrocarbon into an epoxide by oxidation with molecular oxygen include the following problems.

First, the gaseous-phase reaction by the use of molecular oxygen usually requires a reaction temperature of not lower than 200° C. and is therefore not readily applicable to the production of an alcohol, a ketone or an epoxide from a hydrocarbon with high selectivity. This is mainly because it is extremely difficult to optimize the reactivities of oxygen species, especially: 1) when the hydrocarbon is a saturated hydrocarbon, the alcohol or ketone which is the partial oxidation is further oxidized and 2) when the hydrocarbon is unsaturated hydrocarbon, an oxide other than desired one is obtainable (e.g. acrolein is produced instead of an epoxide when the hydrocarbon is propylene).

A number of catalysts recently proposed for increasing the efficiency of the oxidation reaction of hydrocarbons, although low in activity, exhibit high selectivity by activating oxygen in the presence of a reducing agent and effecting a reaction of the enzymatic type capable of inducing in vivo addition of one oxygen atom under relatively mild conditions.

When the Gif catalyst system (reported in J. Chem. Soc. Chem. Commun., 1983, 731, for example), a well-known catalyst system that functions similarly to the one oxygen-atom addition enzyme, is used, for example, the compound mentioned above is produced with high selectivity by oxidizing a saturated hydrocarbon with oxygen by the use of an iron type catalyst in such a proton-donating solvent as acetic acid in the presence of such an electron-donating agent or reducing agent as zinc powder. The use of this catalyst is, however, not practicable, because the production efficiency is extremely low and the reaction system is complicated.

Successful epoxidation of an unsaturated hydrocarbon by the use of an alcohol or an aldehyde as an electron-donating agent have been reported (in Bull. Chem. Soc. Jpn., 1992, 64, 2513, for example). Since the alcohol or aldehyde is oxidized together with the unsaturated hydrocarbon, however, this method has many problems yet to be solved.

Attempts are being made to implement the epoxidation by the use of hydrogen as an inexpensive reducing agent. According to a report in J. Chem. Soc. Chem. Commun., 1992, 1446–1447, the oxidation of a hydrocarbon (hexane in this case) containing a proton source such as hydrochloric acid effected by suspending in the hydrocarbon a catalyst of Pd deposited on titanosilicate and bubbling hydrogen and oxygen through the hydrocarbon produces the corresponding alcohol and ketone with high selectivity. J. Amer. Chem. Soc., 1987, 109, 2837–2839 reports that similar results are obtained when a similar procedure is carried out on hexanes and octanes by the use of a catalyst consisting of Pd and Fe deposited on zeolite. These methods are, however, not practicable in terms of the reaction rate because hydrogen peroxide is produced on the Pd to oxidize a hydrocarbon and because the reaction should be carried out in a liquid phase.

Some of the methods which use a reducing agent as described above are indeed capable of obtaining results satisfactory in terms of selectivity. They are nevertheless unfit for actual use because their production efficiencies are low and their reaction systems are complicated.

A need therefore exists for the development of a method for producing an alcohol, a ketone, and an epoxide at a high selectivity with a high yield by the oxidation of a saturated or an unsaturated hydrocarbon.

The inventors continued a study with a view to providing such a method and accomplished this invention as a result.

SUMMARY OF THE INVENTION

This invention is directed to a method for the selective and effective production of an alcohol or a ketone or a mixture thereof from a saturated hydrocarbon or an epoxide from an unsaturated hydrocarbon by passing a mixture comprising of molecular hydrogen, the saturated or unsaturated hydrocarbon and oxygen through a bed of a catalyst comprising a titanium dioxide carrier and ultrafine gold particles deposited on the carrier, thereby effecting the oxidation of the hydrocarbon with oxygen.

DESCRIPTION OF THE PREFERRED EMBODIMENTS

The salient feature of the method of this invention is that it can be effected by a gaseous-phase heterogeneous catalytic reaction. To be specific, this method can produce a gas containing the desired oxygen-containing compound as a product by passing a mixed gas consisting of hydrogen, oxygen, and a hydrocarbon through the bed of a catalyst containing gold immobilized on a titanium dioxide carrier. This invention for the first time provides a method for producing an alcohol, a ketone, and an epoxide by the oxidation of a hydrocarbon with oxygen in the presence of a reducing agent.

The hydrocarbons which can be used as raw materials in this invention are saturated hydrocarbons having about 3 to 12 carbon atoms and unsaturated hydrocarbons having about 2 to 12 carbon atoms, for example.

The reason for limiting the hydrocarbons usable in this invention to the ranges mentioned above is that hydrocarbons having less than 3 or 2 carbon atoms are stable and are not easily activated and those having more than 12 carbon atoms are susceptible to side reactions.

When the reaction is carried out in a gaseous phase, hydrocarbons having up to about six carbon atoms are suitable as raw materials because the products of the reaction are easily separated from the catalyst bed at low temperatures in the neighborhood of 100° C.

The reason for specifying hydrocarbons having such small numbers of carbon atoms is that the oxygen-containing compounds produced from hydrocarbons having large numbers of carbon atoms have high boiling points, do not desorb easily from the surface of the catalyst, and are susceptible to further oxidation.

Specific examples of usable saturated hydrocarbons include propane, n-butane, isobutane, cyclobutane, n-pentane, 2-methylbutane, cyclopentane, n-hexane, 2-methylpentane, 3-methylpentane and cyclohexane. Specific examples of the unsaturated hydrocarbons include ethylene, propylene, 1-butene, 2-butene, isobutene, 1-pentene, 2-pentene, 2-methyl-1-butene, 3-methyl-1-butene, cyclopentene, 1-hexene, 2-hexene, 3-hexene, 2-methyl-1-pentene, 3-methyl-1-pentene, cyclohexene, 1-methyl-1-cyclopentene, 3-methyl-1-cyclopentene and 4-methyl-1-pentene.

The method of this invention which uses a saturated hydrocarbon as a raw material is characterized by the fact that a ketone is mainly formed when a secondary carbon-hydrogen bond is oxidized and an alcohol is mainly formed when a tertiary carbon-hydrogen bond is oxidized. The reactivity of carbon-hydrogen bonds decreases in the order of tertiary>secondary>primary. The primary carbon-hydrogen bonds hardly undergo the reaction.

As the catalyst used in this invention, it is essential to use gold and titanium dioxide in combination. These two substances jointly bring about a specific and synergistic effect. The catalytic action contemplated by this invention is not manifested when gold and titanium dioxide are used independently.

Since the catalyst containing gold and titanium dioxide has to be constituted as ultrafine gold particles of nanometer-order size immobilized on a titanium dioxide carrier, the method of producing the catalyst is an important factor in the invention. It is preferably produced by the deposition-precipitation or coprecipitation method since a catalyst produced by the ordinary impregnation method does not exhibit the specific catalytic capability required by the invention.

Specifically, the deposition-precipitation method and the coprecipitation method enable the production of a catalyst having ultrafine gold particles deposited relatively uniformly on a titanium dioxide carrier with strong interaction. It is necessary that the ultrafine gold particles of the catalyst have radii of not larger than 10 nm. This is because the length of the perimeter interface between the ultrafine gold particles and titanium dioxide strongly affects the catalytic activity. The length of the peripheral part increases as the radii of the gold particles decrease, i.e., in proportion to the reciprocal of the square of particle radius.

The term "deposition-precipitation method" refers to a method for causing the gold to be deposited and precipitated in the form of hydroxide exclusively on the surface of the carrier by controlling the pH, temperature, etc. of the aqueous solution of a water-soluble gold compound.

The term "coprecipitation method" refers to a method which comprises neutralizing a mixed aqueous solution of a water-soluble gold compound with a raw material for a carrier metal oxide (such as titanium sulfate) thereby producing a mixture of hydroxides, and washing, filtering, and firing the resultant mixture.

Although this invention does not particularly specify the crystal structure, shape, dimensions, etc. of the titanium dioxide carrier, it is generally better to use titanium dioxide of anatase crystal form for the carrier. It is preferable to use for the carrier a titanium dioxide having small diameters of primary particles in the approximate range of 10 to 200 nm and a relatively large specific surface area of not less than 5 $m^2/g$.

The anatase crystal form is preferable because this form has smaller crystallites and a larger specific surface than the rutile crystal form.

The reason for limiting the primary particle diameter to the range of 10 to 200 nm is for ensuring that the carrier acquires a desirably large specific surface and allows easy deposition and precipitation of gold thereon.

The reason for setting the minimum specific surface at 5 $m^2/g$ is that if the specific surface is smaller than 5 $m^2/g$, the carrier will no longer allow easy deposition and precipitation of gold thereon.

The maximum specific surface of the carrier is about 150 $m^2/g$ from the practical point of view.

A catalyst of any other form can function appropriately for the sake of the method of this invention so long as it contains gold and titanium dioxide in the manner described above. So long as the catalyst has ultrafine gold particles deposited on a carrier of titanium dioxide with strong interaction, the function thereof necessary for the operation of this invention is not altered even when this catalyst is immobilized further on a conventional carrier formed of silica, alumina, or the like.

The amount of the catalyst to be used herein is not particularly limited. From the practical point of view, however, it is preferably such that the space velocity (S.V.) of the feed gas through the bed of the catalyst is in the approximate range of 100 to 10000 $hr^{-1} \cdot ml/g \cdot cat$.

In this invention, the presence of hydrogen in the reaction system is essential. If a mixed gas consisting of oxygen and a hydrocarbon and optionally further containing a diluent gas but containing no hydrogen is subjected to the reaction aimed at in the presence of the catalyst mentioned above, the reaction begins to proceed at a temperature of not lower than 200° C. but carbon dioxide is mainly formed and the aforementioned product of partial oxidation is not produced at all. When hydrogen is present in the reaction system, however, the reaction proceeds in a completely different manner. Even at low temperatures in the neighborhood of 50° C., the formation of the aforementioned product of partial oxidation becomes fully evident. The amount of hydrogen present in the reaction system is not particularly limited. From the practical point of view, it is generally such that the volumetric ratio of hydrogen/raw material falls in the approximate range of 1/10 to 100/1. Since the velocity of the reaction generally increases in proportion as the proportion of hydrogen in the volumetric ratio mentioned above increases, it is preferable to select a rather large value within the range mentioned above.

The reaction temperature in this invention falls generally in the approximate range of 0° to 300° C., and preferably in the approximate range of 20° to 200° C. When the reaction is carried out in a gaseous phase, it is necessary to select a temperature at which the product of the reaction manifests ample volatility under the reaction pressure (generally in the approximate range of 0.01 to 1 MPa) so as to facilitate the separation of the product from the catalyst bed. If the reaction temperature is unduly high, the disadvantage arises that the combustion of hydrocarbon, etc. into carbon dioxide will occur readily and, at the same time, the consumption of hydrogen by the oxidation thereof into water will increase. Though the optimum reaction temperature varies with the kind of raw material used, the reaction temperature preferably falls in the approximate range of 20° to 200° C.

The gaseous-phase reaction is implemented by feeding a mixed gas containing a hydrocarbon, hydrogen and oxygen and optionally further containing a diluent gas (such as nitrogen, argon, helium or carbon dioxide) to a reaction column packed with a gold-titanium dioxide-containing catalyst and allowing the ensuing reaction to proceed under prescribed conditions.

From the practical point of view, the molar ratio of molecular hydrogen, hydrocarbon and oxygen in the mixed gas is preferably in the range of 1:0.01–10:0.1–20.

When the reaction aimed at by this invention is carried out in a liquid phase, it can be effected at a temperature of not higher than 100° C. in most cases because this reaction obviates the necessity for taking into consideration the separation of the product from the catalyst bed mentioned above. Alternatively, the reaction in the liquid phase can be carried out either by selecting the reaction pressure and the reaction temperature so as to retain the raw material in a liquid state or by causing a mixed gas consisting of the raw material, hydrogen, oxygen and optionally a diluent gas to bubble through the catalyst suspended in a solvent (such as a hydrocarbon type solvent like benzene or a halogenated hydrocarbon type solvent like methylene chloride).

In the case of the liquid-phase reaction, the molar ratio of hydrogen, hydrocarbon and oxygen in the mixed gas is the same as in the gaseous-phase reaction.

The characteristic features of this invention will now be described more specifically with reference to examples of the preparation of catalyst and working examples of the invention.

EXAMPLE 1 OF CATALYST PREPARATION

Preparation of Gold-Titanium Dioxide Catalyst by Deposition and Precipitation Method (JP-B-06-29,137 and JP-A-06-16,422)

A solution of 0.104 g (0.254 mmol) of chloroauric acid tetrahydrate in 400 ml of distilled water was heated to 70° C., adjusted to pH 7.5 with an aqueous 0.1N NaOH solution, vigorously stirred and in the course of stirring added at one time with 5.0 g of titanium dioxide (anatase form, produced by Japan Aerosil Ltd. and marketed as "P-25"), and continuously stirred at the same temperature for one hour. The resultant reaction solution was cooled, left standing at rest, removed of the consequently separated supernatant, added with 3 liters of distilled water, stirred at room temperature for five minutes, and again left standing at rest and removed of the separated supernatant. This washing operation was repeated three more times. The resultant mixture was filtered. The paste consequently obtained was vacuum dried at room temperature for 12 hours and calcined in the air at 400° C. for four hours, to obtain a gold-titanium dioxide catalyst having 1% by weight of gold deposited thereon.

When the gold-titanium dioxide catalyst thus obtained was observed with a high-resolution electron microscope, it was found to have ultrafine gold particles of 2 to 4 nm in diameter deposited on the surface of titanium dioxide with uniform dispersion.

EXAMPLE 1

Oxidation of Propane with Oxygen

In a U-shaped quartz reaction tube having an inside diameter of 10 mm and provided therein with a sheath of thermocouple, 0.5 g of the gold-titanium dioxide catalyst (70 to 120 mesh) obtained in Example 1 of Catalyst Preparation above was set in place. The reaction tube packed with the catalyst was heated in a water bath until the temperature of the catalyst bed reached 80° C. Then, a mixed gas consisting of hydrogen, oxygen propane and argon (at a volumetric ratio of 10/10/10/70) was passed through the reaction tube at a flow rate of 2000 ml/hr (space velocity of 4000 $hr^{-1}$ ml/g). The outlet gas from the reaction tube was analyzed by gas chromatography to ascertain the results of the reaction.

The results of the reaction are shown in Table 1.

EXAMPLE 2

Oxidation of Isobutane with Oxygen

The oxidation of isobutane was carried out by following the procedure of Example 1 while using isobutane in the place of propane. The results are shown in Table 1.

EXAMPLE 3

Oxidation of Propylene with Oxygen

The oxidation of propylene was carried out by following the procedure of Example 1 while using propylene in the place of propane and changing the temperature of the catalyst bed to 50° C. The results are shown in Table 1.

EXAMPLE 2 OF CATALYST PREPARATION

Example of Preparation of Gold-Titanium Dioxide-Silica Catalyst by Deposition and Precipitation Method Silica (produced by Fuji-Davison K.K. and marketed as "ID Gel") in an organic solvent was impregnated with titanyl acetyl acetonate. The impregnated silica was treated with an evaporator to expel the solvent by distillation, then dried, and calcined in air at 500° C. to obtain titanium dioxide-silica (containing 3% by weight of titanium dioxide of anatase form). Gold was deposited on 5.0 g of the composite by following the procedure of Example 1 of Catalyst Preparation. The resultant composite was dried in the same manner as described above and fired to obtain gold-titanium dioxide-silica.

When the catalyst thus produced was observed with a high-resolution electron microscope by following the procedure of Example 1 of Catalyst Preparation, it was found to have ultrafine gold particles of 2 to 4 nm in diameter deposited on the surface of titanium dioxide with uniform dispersion.

EXAMPLE 4

Oxidation of Propane

In the same apparatus as used in Example 1, 0.5 g of the gold-titanium dioxide-silica catalyst (20–42 mesh) obtained in Example 2 of Catalyst Preparation was set in place. A mixed gas consisting of hydrogen, oxygen, propane, and argon (at a volumetric ratio of 40/10/5/45) was passed at a temperature of 120° C. through the apparatus at a flow rate of 2000 ml/hr (space velocity 4000 hr$^{-1}$ ml/g) to cause the oxidation. The results are shown in Table 1.

EXAMPLE 5

Oxidation of Isobutane with Oxygen

The oxidation of isobutane was effected by following the procedure of Example 4 while using isobutane in the place of propane. The results are shown in Table 1.

EXAMPLE 6

Oxidation of Propylene with Oxygen

The oxidation of propylene was effected by following the procedure of Example 4 while using propylene in the place of propane. The results are shown in Table 1.

The oxidation was found to form absolutely no propylene oxide. When the reaction temperature was raised, consumption of hydrogen by oxidation alone occurred at temperatures up to 100° C. and hydrogenation of propylene into propane occurred at temperatures exceeding 100° C. Thus, absolutely no formation of propylene oxide was observed during the reaction at the elevated temperatures.

COMPARATIVE EXAMPLE 2

Oxidation of Propylene with Oxygen in the Absence of Hydrogen

Oxidation of propylene was attempted by following the procedure of Example 3 while using a mixed gas consisting of oxygen, propylene and argon (at volumetric ratio of 10/10/80) instead.

Absolutely no reaction occurred at temperatures up to 200° C. At temperatures exceeding 200° C., formation of carbon dioxide mainly occurred. Absolutely no formation of propylene oxide was observed at any temperature.

TABLE 1

| Example | Raw material | Reaction temperature (°C.) | Raw Material Conversion (mol %) | Rate of oxidation of raw material (mmol/g · cat/hr) | Selectivity of product | |
|---|---|---|---|---|---|---|
| 1 | Propane | 80 | 0.21 | 0.034 | Acetone | 14.6% |
| 2 | Isobutane | 80 | 0.39 | 0.064 | t-Butanol | 46.0% |
|   |   |   |   |   | Acetone | 10.0% |
| 3 | Propylene | 50 | 1.09 | 0.182 | Propylene oxide | 100% |
| 4 | Propane | 120 | 0.48 | 0.039 | Acetone | 58.8% |
| 5 | Isobutane | 120 | 1.04 | 0.086 | t-Butanol | 84.8% |
|   |   |   |   |   | Acetone | 7.7% |
| 6 | Propylene | 120 | 2.31 | 0.207 | Propylene oxide | 92.9% |

COMPARATIVE EXAMPLE 1 OF CATALYST PREPARATION

Preparation of Gold-Titanium Dioxide Catalyst by Impregnation Method

A solution of 0.104 g (0.254 mmol) of chloroauric acid tetrahydrate in 400 ml of distilled water was added with 5 g of titanium dioxide (produced by Japan Aerosil Ltd. and marketed as "P-25") and treated in an evaporator under a reduced pressure to expel water by distillation. The powder consequently obtained was vacuum dried at room temperature for 12 hours and calcined in air at 400° C. for four hours to obtain a gold-titanium dioxide catalyst having 1% by weight of gold deposited therein (hereinafter referred to as "catalyst for comparison").

When the catalyst for comparison was observed with a high-resolution electron microscope in the same manner as in Example 1 of Catalyst Preparation, it was found that globular gold particles about 20 nm in diameter were dispersed on the surface of titanium dioxide and the particle diameters were distributed over a fairly wide range.

COMPARATIVE EXAMPLE 1

Oxidation of Propylene with Oxygen using Comparative Catalyst

Propylene was oxidized by following the procedure of Example 3 (the reaction temperature at 50° C.) except that 0.5 g of the comparative catalyst was used.

COMPARATIVE EXAMPLE 3

Oxidation of Propylene with Oxygen using Titanium Dioxide

Oxidation of propylene was attempted by following the procedure of Example 3 while using titanium dioxide (produced by Japan Aerosil Ltd. and marketed as "P-25") instead.

Absolutely no reaction occurred in this case at reaction temperatures up to 200° C.

EXAMPLE 7

Liquid-Phase Oxidation

In 20 ml of benzene solvent, 0.5 g of the catalyst obtained in Example 2 of Catalyst Preparation was suspended. A mixed gas consisting of hydrogen, oxygen, propylene and argon (at a volumetric ratio of 10/10/10/70) was bubbled through the suspension at a flow rate of 2000 ml/hr (space velocity 4000 hr$^{-1}$ ml/g ) at a temperature of 40° C. for three hours.

By analyzing the off gas and the catalyst, the treatment was confirmed to have formed 0.080 mmol of propylene oxide. This quantity represents a yield of 1.0%.

What is claimed is:

1. A method for the production of at least one member selected from the group consisting of alcohol, a ketone and mixtures thereof from a saturated hydrocarbon or an epoxide from an unsaturated hydrocarbon by passing a mixture comprising of molecular hydrogen, said saturated or unsaturated hydrocarbon, and oxygen through a bed of a catalyst comprising a titanium dioxide carrier and ultrafine gold particles having a particle radius of no greater than 10 nm deposited on said carrier, thereby effecting the oxidation of said hydrocarbon with oxygen.

2. The method according to claim 1, wherein said catalyst is manufactured by one method selected from the group consisting of deposition-precipitation method and coprecipitation method.

3. The method according to claim 1, wherein said space velocity is in the range of 100 to 10000 $hr^{-1}$ ml/g of catalyst.

4. The method according to claim 1, wherein said titanium dioxide has a crystal form of anatase.

5. The method according to claim 1, wherein the molar ratio of molecular hydrogen, hydrocarbon and oxygen in said mixed gas is in the range of 1:0.01–10:0.1–20.

6. The method according to claim 1, wherein said hydrocarbon is at least one saturated hydrocarbon selected from the group consisting of propane, n-butane, isobutane, cyclobutane, n-pentane, 2-methylbutane, cyclopentane, n-hexane, 2-methylpentane, 3-methylpentane and cyclohexane.

7. The method according to claim 1, wherein said hydrocarbon is at least one unsaturated hydrocarbon selected from the group consisting of ethylene, propylene, 1-butene, 2-butene, isobutene, 1-pentene, 2-pentene, 2-methyl-1-butene, 3-methyl-1-butene, cyclopentene, 1-hexene, 2-hexene, 3-hexene, 2-methyl-1-pentene, 3-methyl-1-pentene, cyclohexene, 1-methyl-1-cyclopentene, 3-methyl-1-cyclopentene and 4-methyl-1-pentene.

\* \* \* \* \*